US010738097B2

(12) United States Patent
Poorebrahim et al.

(10) Patent No.: US 10,738,097 B2
(45) Date of Patent: Aug. 11, 2020

(54) INTERFERON-BETA ANALOG PEPTIDE

(71) Applicants: Mansour Poorebrahim, Tehran (IR); Matin Asghari, Isfahan (IR); Mohammad Hossein Nasr-Esfahani, Isfahan (IR); Nima Sanadgol, Zahedan (IR); Mohammad Foad Abazari, Tehran (IR); Maryam Nouri Aleagha, Tehran (IR); Hassan Askari, Tehran (IR); Solmaz Sadeghi, Tehran (IR)

(72) Inventors: Mansour Poorebrahim, Tehran (IR); Matin Asghari, Isfahan (IR); Mohammad Hossein Nasr-Esfahani, Isfahan (IR); Nima Sanadgol, Zahedan (IR); Mohammad Foad Abazari, Tehran (IR); Maryam Nouri Aleagha, Tehran (IR); Hassan Askari, Tehran (IR); Solmaz Sadeghi, Tehran (IR)

( * ) Notice: Subject to any disclaimer, the term of this patent is extended or adjusted under 35 U.S.C. 154(b) by 0 days.

(21) Appl. No.: 16/151,357

(22) Filed: Oct. 4, 2018

(65) Prior Publication Data
US 2019/0092832 A1 Mar. 28, 2019

Related U.S. Application Data

(60) Provisional application No. 62/569,627, filed on Oct. 9, 2017.

(51) Int. Cl.
*C07K 14/565* (2006.01)
*A61K 38/00* (2006.01)

(52) U.S. Cl.
CPC ............ *C07K 14/565* (2013.01); *A61K 38/00* (2013.01)

(58) Field of Classification Search
None
See application file for complete search history.

(56) References Cited

U.S. PATENT DOCUMENTS

| 6,127,332 A | 10/2000 | Goelz et al. |
| 8,057,787 B2 | 11/2011 | Gantier et al. |
| 8,329,869 B2 | 12/2012 | Kraynov et al. |

OTHER PUBLICATIONS

Poorebrahim, Immunomodulatory effects of a rationally designed peptide mimetic of human IFNβ in EAE model of multiple sclerosis, Progress in Neuropsychopharmacology & Biological Psychiatry, 2018, vol. 82, pp. 49-61.

*Primary Examiner* — Daniel E Kolker
*Assistant Examiner* — Jegatheesan Seharaseyon
(74) *Attorney, Agent, or Firm* — Bajwa IP Law Firm; Harris Zaheer Bajwa

(57) ABSTRACT

An interferon-beta (IFNβ) analog peptide including a plurality of amino acid substitutions in an amino acid sequence of IFNβ as set forth in SEQ ID No. 4. The IFNβ analog peptide may include a plurality of amino acid substitution in the amino acid sequence of IFNβ in at least one position of 5, 6, 7, 8, 9, 10, 11, 12, 13, 14, 15, 18, 19, 20, 21, 22, 23, 24, and combinations thereof, numbered in accordance with SEQ ID No. 4.

4 Claims, 17 Drawing Sheets
Specification includes a Sequence Listing.

```
┌─────────────────────────────────────────────────────────────┐
│ Identifying a highly conserved sequence in the amino acid   │──── 102
│ sequence of IFN-β                                           │
└─────────────────────────────────────────────────────────────┘
                              │
                              ▼
┌─────────────────────────────────────────────────────────────┐
│ Generating a library of tolerated peptides by substituting  │──── 104
│ an amino acid in the amino acid sequence of the highly      │
│ conserved peptide                                           │
└─────────────────────────────────────────────────────────────┘
                              │
                              ▼
┌─────────────────────────────────────────────────────────────┐
│ Selecting the IFNβ analog peptide by improving binding      │──── 106
│ affinity and stability of the tolerated peptides            │
└─────────────────────────────────────────────────────────────┘
```

INTERFERON-BETA ANALOG PEPTIDE

CROSS-REFERENCE TO RELATED APPLICATION

This application claims the benefit of priority from U.S. Provisional Patent Application Ser. No. 62/569,627, filed on 2017 Oct. 9, and entitled "A Peptide Mimetic of Human IFNβ for Treatment of Multiple Sclerosis (MS)," which is incorporated herein by reference in its entirety.

TECHNICAL FIELD

The present disclosure generally relates to peptide-based drugs, particularly to interferon beta (IFNβ) analog peptides, and more particularly to IFNβ analog peptides for treatment of multiple sclerosis (MS).

BACKGROUND

Multiple sclerosis (MS) is an autoimmune disease which may attack the myelin proteins in the central nervous system (CNS). One of the most important hallmarks of the MS process is that peripherally activated inflammatory cells may pass across the blood-brain barrier (BBB) leading to demyelination within the CNS. Numerous studies have been undertaken to understand the key inflammatory mediators and neurodegenerative mechanisms that underlie the relapsing and progressive phase of the disease.

Interferon-beta (IFNβ)-based formulations have been shown to alleviate the exacerbations of MS and may be used as a first-line treatment for relapsing-remitting multiple sclerosis (RRMS). However, IFNβ-based therapy may lead to a number of adverse side effects including flu-like symptoms, inconsistencies in patient laboratory analyses, menstrual disorders, and increased spasticity. Moreover, similar to other clinically available protein-based drugs, IFNβ has several drawbacks including a high number of antigenic regions, high cost, and susceptibility to proteolytic degeneration.

Peptide-based drugs have several unique physicochemical properties that make them attractive in medical interventions. Since peptides may be suitable alternatives of IFNβ for treatment of MS, there is a need for an IFNβ analog peptide with improved physicochemical properties, lower number of antigenic regions, lower cost, and higher stability. Moreover, there is a need for an IFNβ analog peptide for the treatment of MS without IFNβ side effects.

SUMMARY

This summary is intended to provide an overview of the subject matter of the exemplary embodiments of the present disclosure, and is not intended to identify essential elements or key elements of the subject matter, nor is it intended to be used to determine the scope of the claimed implementations. The proper scope of the exemplary embodiments of the present disclosure may be ascertained from the claims set forth below in view of the detailed description below and the drawings.

In one general aspect, the present disclosure describes an exemplary interferon-beta (IFNβ) analog peptide including a plurality of amino acid substitutions in an amino acid sequence of IFNβ as set forth in SEQ ID No. 4. The IFNβ analog peptide may include a plurality of amino acid substitution in at least one position of 5, 6, 7, 8, 9, 10, 11, 12, 13, 14, 15, 18, 19, 20, 21, 22, 23, 24, and combinations thereof, numbered in accordance with SEQ ID No. 4.

The above general aspect may include one or more of the following features. In some exemplary embodiments, the IFNβ analog peptide may include at least one of I5F, F6R, I8G, F9W, R10H, D12N, S13T, S14L, S15N, W18L, N19R, E20W, T21V, I22G, V23F amino acid substitutions, and combinations thereof, in the amino acid sequence of IFNβ. In some exemplary embodiments, the IFNβ analog peptide may have an amino acid sequence as set forth in SEQ ID No. 1.

According to some exemplary embodiments, the IFNβ analog peptide may include at least one of I5G, F6R, A7D, I8V, F9R, R10K, Q11R, D12G, S13F, S15D, W18L, N19R, E20K, T21L, I22G, V23R, E24V amino acid substitutions, and combinations thereof in the amino acid sequence of IFNβ with SEQ ID No. 4. In some exemplary embodiments, the IFNβ analog peptide may have an amino acid sequence as set forth in SEQ ID No. 2

According to some exemplary embodiments, the IFNβ analog peptide may include at least one of I5G, F6R, I8L, F9R, R10K, D12N, S13F, S14L, S15N, W18L, N19R, E20K, T21L, I22G, V23H amino acid substitutions, and combinations thereof in the amino acid sequence of IFNβ with SEQ ID No. 4. In some exemplary embodiments, the IFNβ analog peptide may have an amino acid sequence as set forth in SEQ ID No. 3. In some exemplary embodiments, the IFNβ analog peptide may include about 27 amino acids. In some exemplary embodiments, the IFNβ analog peptide may have an antiviral activity and an immunomodulatory activity including suppressing pro-inflammation mediators.

In another general aspect, the present disclosure describes an exemplary method for treating multiple sclerosis (MS) and viral infections in a patient. The method may include administering an effective amount of the IFNβ analog peptide. The IFNβ analog peptide may include a plurality of amino acid substitution in at least one position of 5, 6, 7, 8, 9, 10, 11, 12, 13, 14, 15, 18, 19, 20, 21, 22, 23, 24, and combination thereof, numbered in accordance with SEQ ID No. 4.

According to some exemplary embodiments, the effective amount of the IFNβ analog peptide may be between about 10 mg/kg of body weight and about 20 mg/kg of body weight. In some exemplary embodiments, administering the effective amount of the IFNβ analog peptide may include intravenously injecting the effective amount of the IFNβ analog peptide to the patient.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 1 illustrates a method for producing an interferon-beta (IFNβ) analog peptide, consistent with one or more exemplary of the present disclosure.

DETAILED DESCRIPTION

Figure 2A:
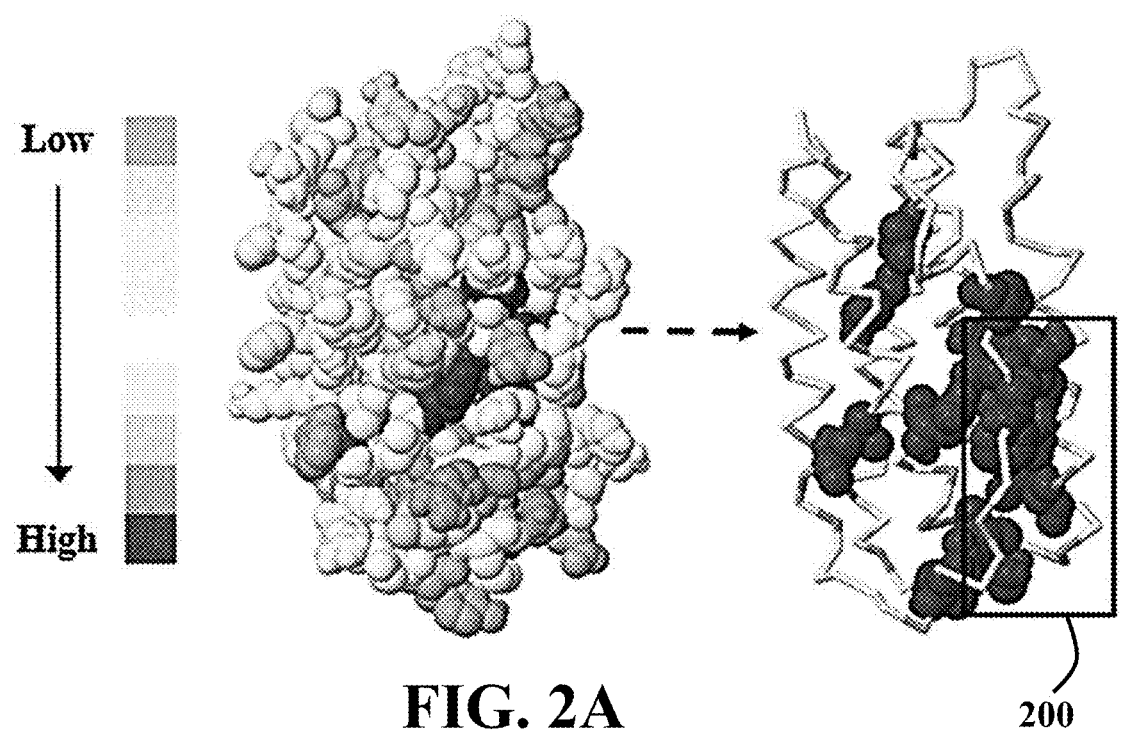
FIG. 2A illustrates a representation of IFNβ structure with cross-species conservation scores, consistent with one or more exemplary embodiments of the present disclosure.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Interferons may initiate specific signals via formation of heterodimeric IFNAR1-IFNAR2 complexes. However, interferon-beta (IFNβ) may be able to induce intracellular signals through binding to IFNAR1, independent of interferon-alpha/beta receptor beta chain (IFNAR2). Thus, IFNβ may be a promising candidate for designing analog peptides in MS therapy without targeting the IFNAR2. However, efficiency of IFNβ-based drugs may be considerably limited due to their undesirable properties, especially high immunogenicity.

In the present disclosure, an exemplary IFNβ analog peptide may be capable of significantly reducing brain dysfunction in MS by down-regulating production of inflammatory mediators. Disclosed herein is the exemplary IFNβ analog peptide including a plurality of amino acid substitutions in an amino acid sequence of IFNβ as set forth in SEQ ID No. 4. The IFNβ analog peptide may include a plurality of amino acid substitution in at least one position of 5, 6, 7, 8, 9, 10, 11, 12, 13, 14, 15, 18, 19, 20, 21, 22, 23, 24, and combinations thereof, numbered in accordance with SEQ ID No. 4.

FIG. 1 shows method 100 for identifying the exemplary IFNβ analog peptide, consistent with one or more exemplary embodiments of the present disclosure. Method 100 may include identifying a highly conserved peptide in an amino acid sequence of IFNβ (step 102), generating a library of tolerated peptides by substituting an amino acid in the highly conserved peptide (step 104), and selecting an exemplary IFNβ analog peptide by improving binding affinity and stability of the tolerated peptides (step 106).

Step 102 may include identifying the highly conserved peptide in the amino acid sequence of IFNβ. In some exemplary implementations, identifying the highly conserved peptide in the amino acid sequence of IFNβ may include identifying conserved residues in the amino acid sequence of IFN-β, predicting functional residues of IFN-β, determining mode of interaction of an IFNβ-IFNAR1 complex, and identifying functionally interacting residues of IFNβ and IFNAR1.

In some exemplary implementations, the highly conserved peptide in the amino acid sequence of IFNβ may be identified using a multiple sequence alignment (MSA) of human IFNβ, mouse IFNβ, and rat IFNβ. In some exemplary embodiments, the MSA may be conducted using at least one of Clustal-W program, ConSurf program, or combinations thereof. In some exemplary implementations, the functional residues of IFNβ which may be involved in IFNβ activity may be predicted by identifying highly conserved patches of three-dimensional (3D) structure of the IFNβ. In some exemplary embodiments, the functional residues of IFNβ may be predicted using the ConSurf program and molecular docking.

In some exemplary embodiments, the mode of interaction of the human IFNβ-IFNAR1 complex may be determined by evaluating the mode of interaction for the murine Ifnβ-Ifnar1 complex and identifying the structurally conserved residues between the human and murine proteins. In some exemplary embodiments, the human IFNβ and murine Ifnβ may be structurally aligned using SuperPose and TM-align servers. In some exemplary embodiments, structures of human IFNAR1 and murine Ifnar1 may be aligned using SuperPose and TM-align servers.

In some exemplary implementations, identifying the functionally interacting residues of IFNβ and IFNAR1 may include determining a ligand-binding site of human IFNAR1 and an IFNAR-binding site of human IFNβ. In some exemplary implementations, the functionally interacting residues of IFNβ and IFNAR1 may be identified using molecular docking and choosing protein complexes with the lowest binding energy. In some exemplary embodiments, molecular docking may be done utilizing at least one of ClusPro web tool, HADDOCK web tool, FlexPepDock web tool, and combinations thereof. In some exemplary embodiments, the highly conserved peptide may include about 27 amino acids of the IFNβ at positions from about 83 to about 109. In some exemplary embodiments, the highly conserved peptide may have an amino acid sequence as set forth in SEQ ID No. 4 and may be one of the most important regions involved in interaction of IFNβ with IFNAR1.

Step 104 may include generating the library of tolerated peptides by substituting the amino acid in the highly conserved sequence. In some exemplary embodiments, the library of tolerated peptides may be generated using Backrub and sequence tolerance protocols implemented in Rosetta package based on IFNAR1-binding site of the IFNβ. It should be noted that functional residues involved in interaction with IFNAR1 and in the biological activity of the IFNβ may not be substituted. In some exemplary embodiments, the most tolerated peptides may be selected from the library of tolerated peptides by in-silico screening.

In some exemplary implementations, substituting the amino acid in the highly conserved peptide may lead to improving physicochemical properties of the highly conserved sequence. In one or more exemplary embodiments, the physicochemical properties may include molecular weight, theoretical isoelectric point (pI), net charge at pH level about 7, instability index, grand average of hydropathicity (GRAVY), number of aggregation hot spots, number of antigenic regions, half-life, water solubility, and cell-penetrating capability.

Step 106 may include selecting the IFNβ analog peptide by improving binding affinity and stability of the tolerated peptides. In some exemplary implementations, selecting the IFNβ analog peptide may include selecting candidate peptides by improving binding affinity of the tolerated peptide and selecting the most stable candidate peptides by calculating free energy of the candidate peptides.

In some exemplary implementations, improving binding affinity of the tolerated peptides may include docking the tolerated peptide with IFNAR1 and selecting candidate peptides with high binding affinity. In some exemplary implementations, improving stability of the tolerated peptides may include calculating free energy and selecting the most stable candidate peptides.

In some exemplary embodiments, the IFNβ analog peptide may include the amino acid substitution in at least one position of 5, 6, 7, 8, 9, 10, 11, 12, 13, 14, 15, 18, 19, 20, 21, 22, 23, 24, and combinations thereof, numbered in accordance with SEQ ID No. 4. In some exemplary embodiments, the IFNβ analog peptide may include the amino acid substitution in the amino acid sequence of the IFNβ including at least one of I5F, F6R, I8G, F9W, R10H, D12N, S13T, S14L, S15N, W18L, N19R, E20W, T21V, I22G, V23F, and combinations thereof. In some exemplary embodiments, the IFNβ analog peptide may have an amino acid sequence as set forth in SEQ ID No. 1.

In some exemplary embodiments, the IFNβ analog peptide may include the amino acid substitution in the amino acid sequence of the IFNβ including at least one of I5G, F6R, A7D, I8V, F9R, R10K, Q11R, D12G, S13F, S15D, W18L, N19R, E20K, T21L, I22G, V23R, E24V, and combinations thereof. In some exemplary embodiments, the IFNβ analog peptide may have an amino acid sequence as set forth in SEQ ID No. 2.

In some exemplary embodiments, the IFNβ analog peptide may include the amino acid substitution in the amino acid sequence of the IFNβ including at least one of I5G, F6R, I8L, F9R, R10K, D12N, S13F, S14L, S15N, W18L, N19R, E20K, T21L, I22G, V23H, and combinations thereof. In some exemplary embodiments, the IFNβ analog peptide may have an amino acid sequence as set forth in SEQ ID No. 3. In some exemplary embodiments, the IFNβ analog peptide may include 27 amino acids.

In some exemplary embodiments, the IFNβ analog peptide may have an antiviral activity and an immunomodulatory activity including suppressing pro-inflammation mediators. In some exemplary embodiments, the IFNβ analog peptide may be used for treating multiple sclerosis (MS) and viral infections in a patient by administering an effective amount of an IFNβ analog peptide.

In some exemplary embodiments, the IFNβ may be used for treating relapsing-remitting multiple sclerosis (RRMS). In some exemplary embodiments, the effective amount of the IFNβ analog peptide may be between about 10 mg/kg of body weight and about 20 mg/kg of body weight. In some exemplary embodiments, administering the effective amount of the IFNβ analog peptide may include intravenously injecting the IFNβ analog peptide.

EXAMPLES

Example 1: Identifying an IFNβ Analog Peptide

In this example, an exemplary IFNβ analog peptide was identified. At first, a highly conserved peptide in the amino acid sequence of IFNβ was identified by identifying conserved residues in the amino acid sequence of IFN-β, predicting functional residues of IFN-β, determining a mode of interaction of the IFNβ-IFNAR1 complex, and identifying functionally interacting residues of IFNβ and IFNAR1.

In order to identify the highly conserved peptide in the amino acid sequence of IFNβ, amino acid sequences of IFNβ in human, mouse, and rat were obtained from UniProt databank. Subsequently, multiple sequence alignment (MSA) was performed using Clustal-W program and the aligned sequences were visualized using the Jalview program. Based on the results of sequence alignment, a peptide including amino acid residues at positions from 83 to 109 of the IFNβ was considered as a highly conserved peptide with an amino acid sequence as set forth in SEQ ID No. 4. The highly conserved peptide included 27 amino acids.

Also, the functional residues of IFNβ involved in IFNβ activity were predicted by identifying highly conserved patches of three-dimensional (3D) structure of the IFNβ using ConSurf server. FIG. 2A shows a representation of IFNβ structure with cross-species conservation scores, consistent with one or more exemplary embodiments of the present disclosure. Referring to FIG. 2A, darker colors/shades indicate more conserved residues, so it may be concluded that highly conserved peptide 200 with the amino acid sequence as set forth in SEQ ID No. 4 included several functionally and structurally conserved residues that were expected to have a central role in interaction of the IFNβ and the IFNAR1.

The mode of interaction of the human IFNβ-IFNAR1 complex was determined by evaluating the mode of interaction for the murine Ifnβ-Ifnar1 complex and identifying the structurally conserved residues between the human and murine proteins. Moreover, the human IFNβ and murine Ifnβ were structurally aligned using SuperPose and TM-align servers. A structural alignment was also carried out between human IFNAR1 and murine Ifnar1.

Figure 2B:
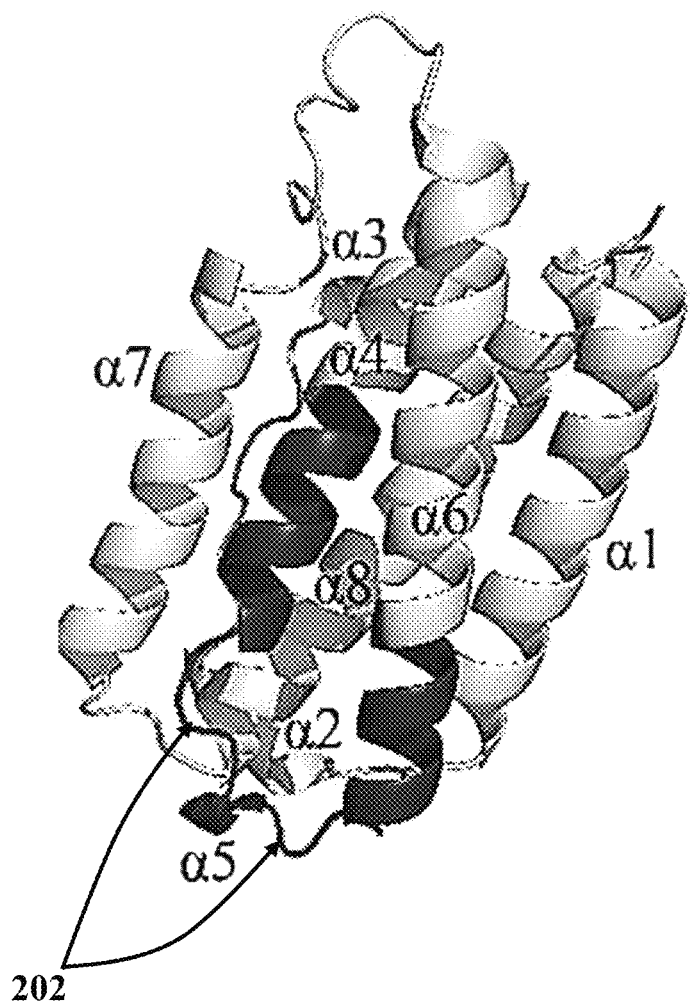
FIG. 2B illustrates a representation of a highly conserved region of IFNβ, consistent with one or more exemplary embodiments of the present disclosure.

FIG. 2B shows a representation of the highly conserved region in the IFNβ structure, consistent with one or more exemplary embodiments of the present disclosure. The highly conserved peptide is shown in black color. Referring to FIG. 2B, the main IFNAR-binding site of IFNβ encompasses a side of IFNβ that is built up by α-helices 4, 5 and 6, and two loop spacers 202.

Furthermore, molecular docking was conducted for determining the functionally interacting residues including a ligand-binding site of human IFNAR1 and an IFNAR-binding site of human IFNβ utilizing ClusPro and HADDOCK web tools. Consequently, both blind and high-resolution docking runs were separately performed, and the protein complexes with lowest binding energy were chosen and visualized using LigPlot+ software to understand the functionally interacting residues of IFNβ and IFNAR1.

Figure 2C:
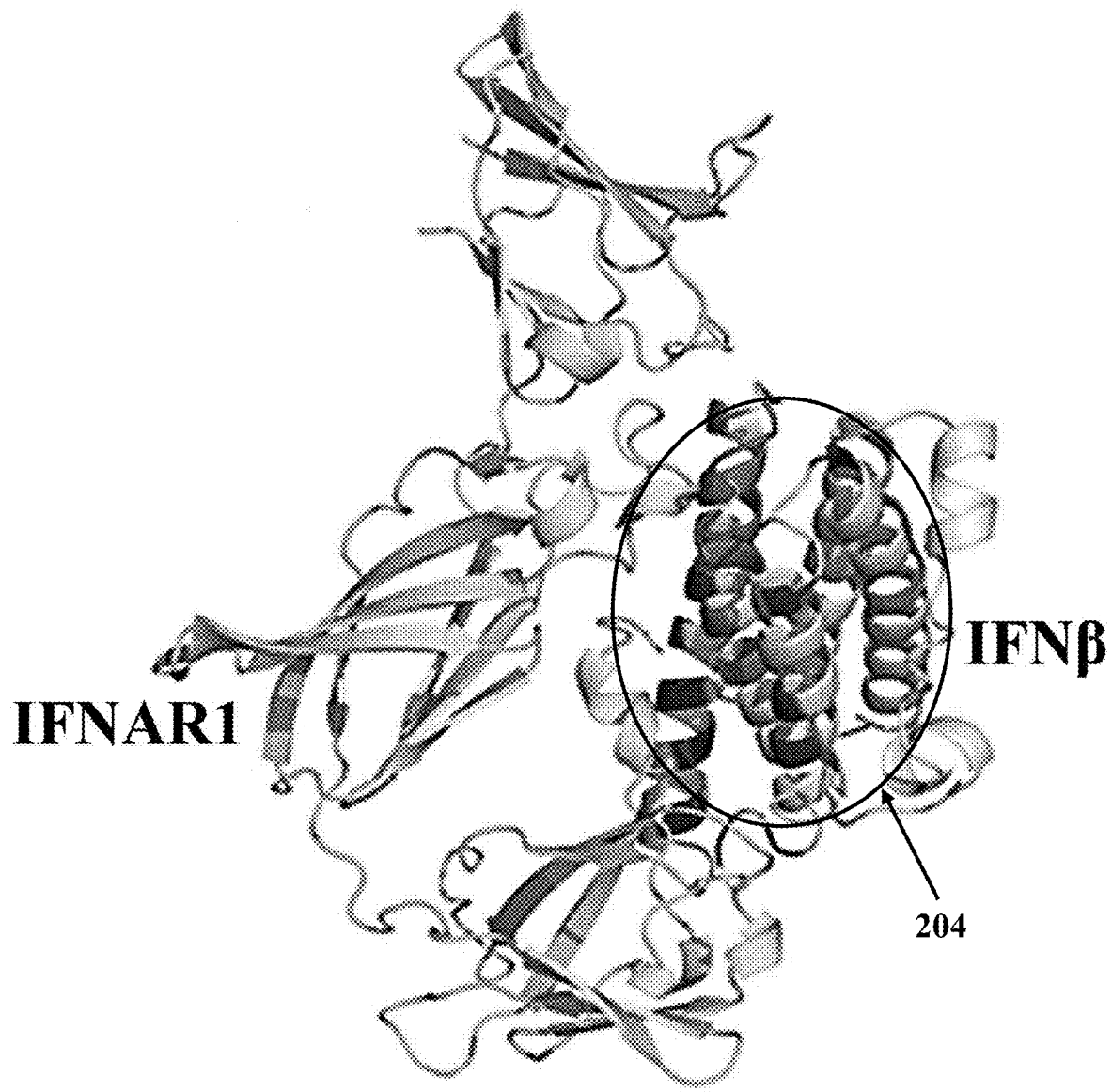
FIG. 2C illustrates a human IFNβ-interferon-alpha/beta receptor alpha chain (IFNAR1) complex after molecular docking, consistent with one or more exemplary embodiments of the present disclosure

FIG. 2C shows a human IFNβ-IFNAR1 complex after molecular docking, consistent with one or more exemplary embodiments of the present disclosure. Referring to FIG. 2C, the residues of the highly conserved peptide were apparently involved in the binding of IFNβ 204 to IFNAR1.

In the next step, the library of tolerated peptides was generated by substituting the amino acid in the highly conserved sequence. The library of tolerated peptides was generated using Rosetta backrub with sequence tolerance protocols implemented in the Rosetta3.5 software based on IFNAR1-binding site of the IFNβ and the most tolerated peptide was determined among hundreds of generated peptides.

Physicochemical properties of the highly conserved peptide were improved via several amino acid substitutions. Physicochemical features such as theoretical pI, net charge at pH 7, grand average of hydropathicity (GRAVY), half-life, and cell-penetrating capability were calculated using ProtParam web tool, Innovagen web tool, and CellPPD web tool. Critical functional residues involved in interaction with IFNAR1 and in the biological activity of the IFNβ were not substituted. Calculation of the physicochemical properties of the highly conserved peptide with SEQ ID No. 4 revealed some undesirable features. Thus, several properties of the highly conserved peptide were improved using some logical amino acid substitutions to derive the IFNβ analog peptide with SEQ ID No. 1 and the IFNβ analog peptide with SEQ ID No. 2.

In the last step, the IFNβ analog peptide was selected by improving binding affinity and stability of the tolerated peptides. At first, candidate peptides were selected by improving binding affinity of the tolerated peptide via docking the tolerated peptide with IFNAR1. Afterward, the most stable candidate peptide as the IFNβ analog peptide was selected by calculating free energy of the candidate peptides. The IFNβ analog peptide included the amino acid substitutions of I5F, F6R, I8G, F9W, R10H, D12N, S13T, S14L, S15N, W18L, N19R, E20W, T21V, I22G, and V23F in the amino acid sequence of the IFNβ. The IFNβ analog peptide had an amino acid sequence as set forth in SEQ ID No. 1 with 27 amino acids.

Figure 3A:
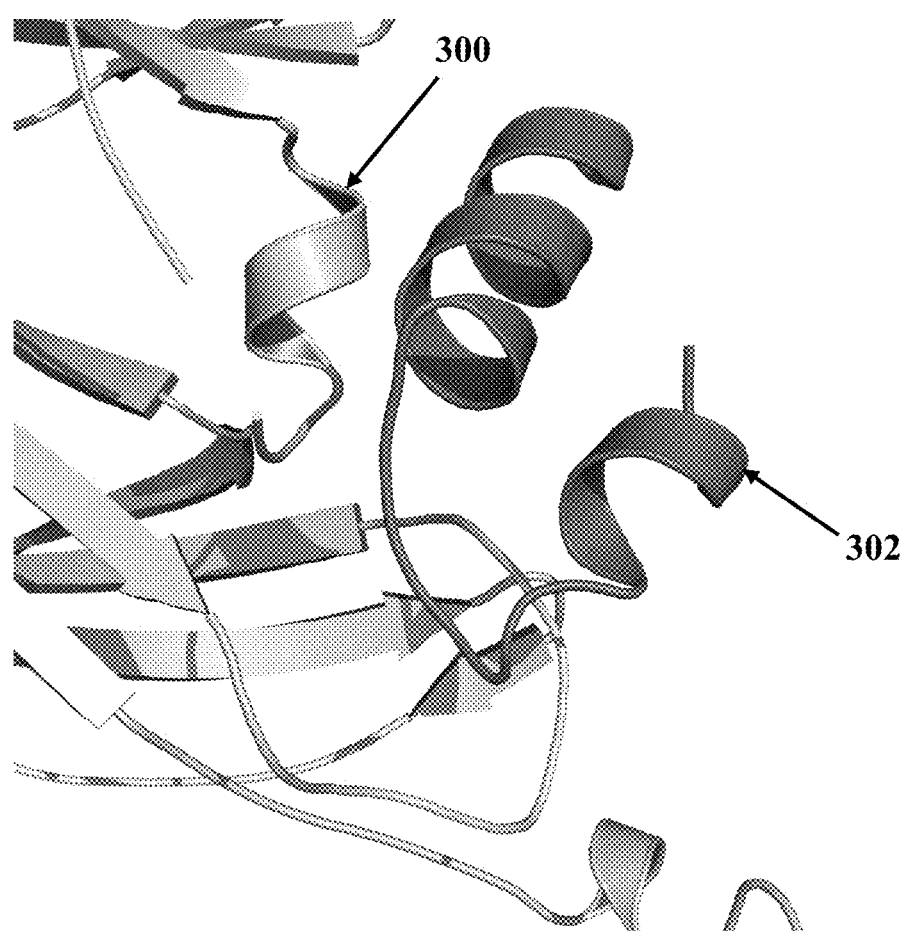
FIG. 3A illustrates an interaction mode between a highly conserved peptide and IFNAR1 after a high-resolution peptide-protein docking, consistent with one or more exemplary embodiments of the present disclosure.
Figure 3B:
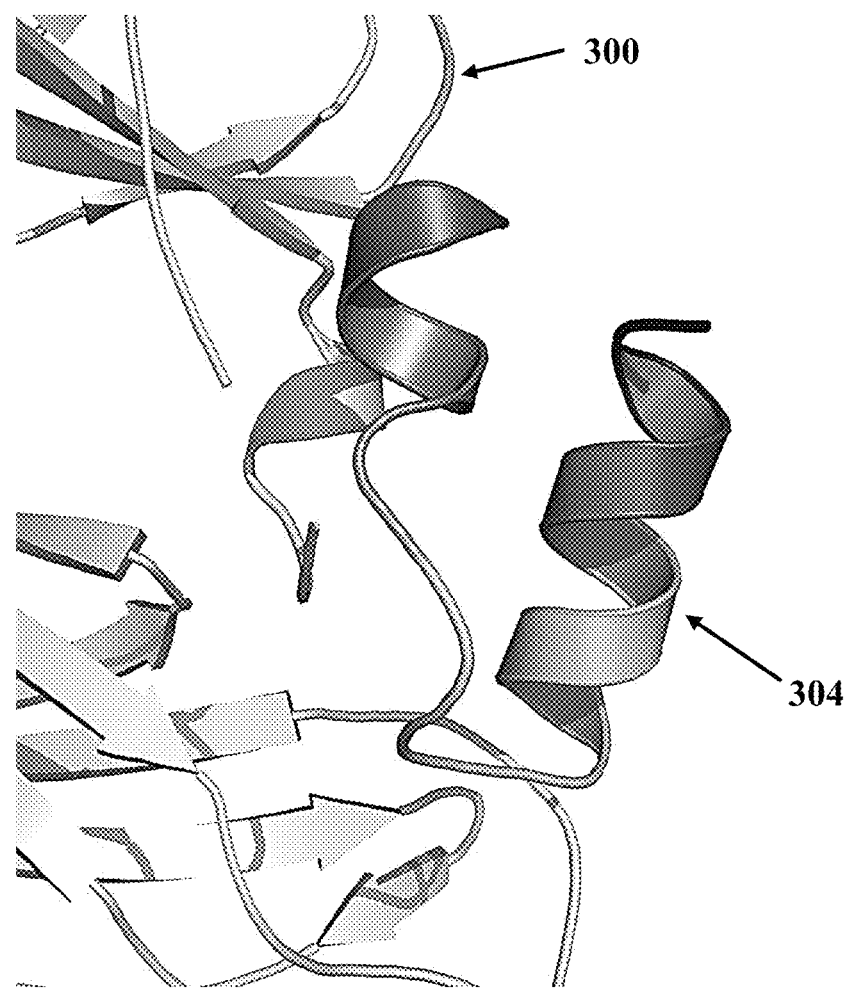
FIG. 3B illustrates an interaction mode between the IFNβ analog peptide and IFNAR1 after a high-resolution peptide-protein docking, consistent with one or more exemplary embodiments of the present disclosure.
Figure 4A:
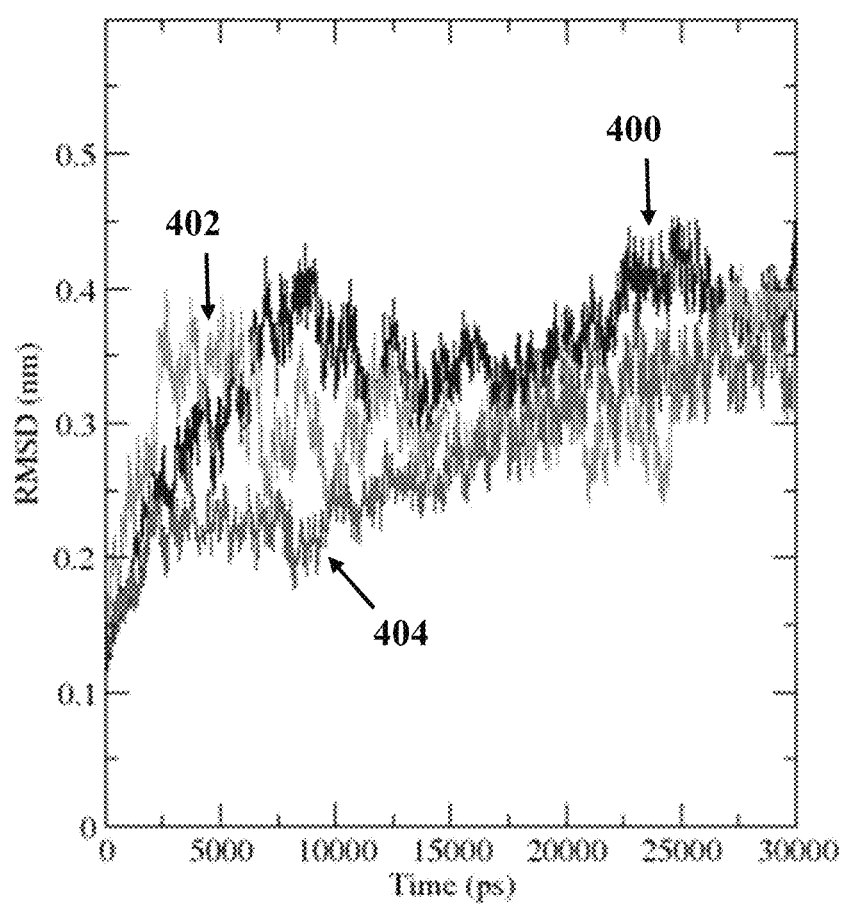
FIG. 4A illustrates a plotted root mean square deviation (RMSD) plot for complexes of different peptides with IFNAR1, consistent with one or more exemplary embodiments of the present disclosure.
Figure 4B:
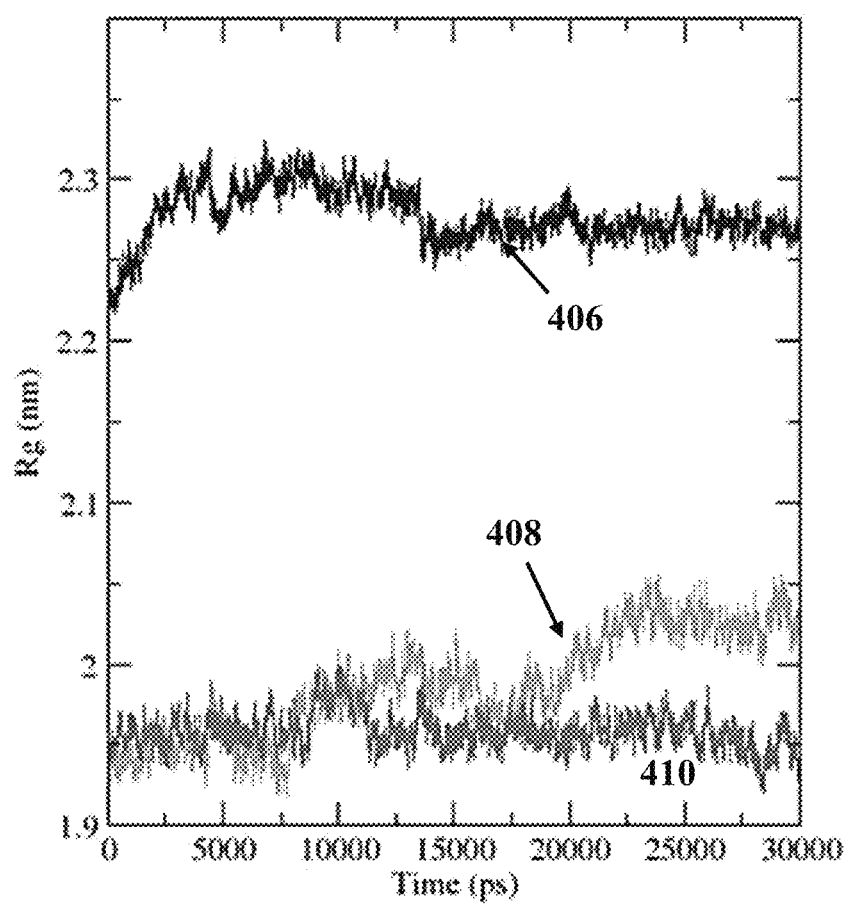
FIG. 4B illustrates a radius of gyration (Rg) plot for complexes of different peptides with IFNAR1, consistent with one or more exemplary embodiments of the present disclosure.

After selecting the IFNβ analog peptide, a high-resolution docking was conducted based on three-dimensional structures of peptides, predominant binding sites, and computational docking information. FIG. 3A shows interaction mode between highly conserved peptide 302 and IFNAR1 300 after a high-resolution peptide-protein docking, consistent with one or more exemplary embodiments of the present disclosure. FIG. 3B shows interaction mode between IFNβ analog peptide 304 and IFNAR1 300 after a high-resolution peptide-protein docking, consistent with one or more exemplary embodiments of the present disclosure.

Referring to FIGS. 3A and 3B, IFNβ analog peptide 304, similar to highly conserved peptide 302, could specifically bind to the ligand-binding site of IFNAR1 300. Regarding the fact that highly conserved peptide 302 of IFNβ may activate the IFNAR signaling through interaction with IFNAR1 300, independent of IFNAR2, IFNβ analog peptide 304 may be capable of inducing downstream signaling through binding to IFNAR1 300. Due to its higher coil structure content, IFNβ analog peptide 304 may be flexible enough to move readily on the receptor surface, and thereby, form a stable peptide-receptor complex.

Also, polar and nonpolar contacts of the complexes were determined. The PRODIGY web tool calculates a number of interfacial contacts (ICs) and percentage of the non-interacting surface (NIS) in a protein-protein complex which has been shown to be crucial in physical protein-protein interactions.

TABLE 1

Number of interfacial contacts (ICs) in the complex of different peptides with IFNAR1

| Type of the IC | Highly conserved peptide-IFNAR1 complexes | IFNβ analog peptide-IFNAR1 complexes |
|---|---|---|
| Charged-Charged | 4 | 5 |
| Charged-Polar | 5 | 8 |
| Charged-Apolar | 11 | 10 |
| Polar-Polar | 2 | 9 |
| Polar-Apolar | 8 | 19 |
| Apolar-Apolar | 19 | 10 |
| Total | 49 | 61 |

Referring again to TABLE. 1, the number of interfacial contacts (ICs), particularly polar-apolar and charged-polar contacts, between the IFNβ analog peptide and IFNAR1 was substantially higher than the highly conserved peptide and IFNAR1. A total number of connections in the IFNβ analog peptide-IFNAR1 complex (61 contacts) were obviously higher than the highly conserved peptide-IFNAR1 complex (49 contacts) indicating that the IFNβ analog peptide with SEQ ID No. 1 may probably form a stable interaction compared to the highly conserved peptide.

Example 2: Interaction Stability of the IFNβ Analog Peptide

In this example, interaction stability of the IFNβ analog peptide with SEQ ID No. 2 was evaluated using molecular dynamics (MD) and energetic analysis. MD simulations were performed using GROMACS package. At first, three-dimensional structure of the highly conserved peptide with SEQ ID No. 4 and IFNβ analog peptide with SEQ ID No. 2 in complex with IFNAR1 were solvated in a solvation box with 10.5 Å distance between the edges of the box and the protein fragments. $Na^+$ and $Cl^-$ ions were added to the box to neutralize the system. Also, SYR6 peptide as a known IFNβ analog peptide was used as a positive control.

Subsequently, the entire systems were minimized and equilibrated for 100 ps using canonical (NVT) and the isothermal-isobaric (NPT) ensembles. Then, the systems were subjected to a 30 ns MD simulation using the leap-frog algorithm with an integration time step of 0.002 ps. Stability and conformational changes of the IFNβ analog peptide-IFNAR1 complex as well as the IFNβ-IFNAR1 complex were assessed using plotted root mean square deviation (RMSD) of the backbone atoms and radius of gyration (Rg).

FIG. 4A shows a plotted root mean square deviation (RMSD) plot for the complex of different peptides with IFNAR1, consistent with one or more exemplary embodiments of the present disclosure. Referring to FIG. 4A, very small, RMSD values, about 0.25 nm at the first 15 nanoseconds (ns) and about 0.3 nm in the second 15-ns of MD simulations, and invariable RMSD values of the IFNβ analog peptide-IFNAR1 complex 404 imply a high stability and low conformational freedom of the peptide-receptor complex during MD simulations. In contrast, RMSD of SYR6-IFNAR1 complex 402 exhibited some structural fluctuations upon binding to IFNAR1 that may be attributed to unstable structure of SYR6-IFNAR1 complex 402.

FIG. 4B shows a radius of gyration (Rg) plot for the complex of different peptides with IFNAR1, consistent with one or more exemplary embodiments of the present disclosure. Referring to FIG. 4B, the Rg value of IFNβ-IFNAR1 complex 406 increased to about 2.3 nm, then decreased to stabilized at about 2.25 nm. The Rg value of SYR6-IFNAR1 complex 408 exhibited a sharp increase from about 2 nm to about 2.05 nm at 20 ns and then stabilizes around this value. The Rg of the IFNβ analog peptide-IFNAR1 complex 410 remained approximately 1.95 nm over the 30 ns MD simulations except for a short period.

Example 3: Binding Affinity of the IFNβ Analog Peptide

In this example, binding affinity of the highly conserved peptide with SEQ ID No. 4 and the IFNβ peptide with SEQ ID No. 2 (MSPEP27) to IFNAR1 was investigated using molecular docking and energetic analysis. At first, an average structure was prepared for each peptide-IFNAR1 complexes from the last 3 ns MD simulations and subjected to the PRODIGY web tool for calculating the ΔG of interactions.

Also, polar and nonpolar contacts of the complexes were determined. The PRODIGY web tool calculates the number of interfacial contacts (ICs) and the percentage of the non-interacting surface (NIS) in a protein-protein complex which has been shown to be crucial in physical protein-protein interactions. In parallel, electrostatic energies were calculated using the PBEQ-Solver tool utilizing 31 snapshot configurations taken from the last 3 nanoseconds (ns) MD productions of the peptide-IFNAR1 complexes and subsequently averaging the values. The van der Waals (VdW) energies were calculated using a standard GROMACS utility.

TABLE 2

Binding energies between different peptides and IFNAR1

| Energy | Highly conserved peptide | IFNβ analog peptide | IFNβ |
|---|---|---|---|
| Interaction Free Energy Components in complex with IFNAR1 (kcal/mol) | | | |
| ClusPro score | −1801.2 | −2447.2 | −2810.4 |
| HADDOCK score | −78.0 ± 8.9 | −147.3 ± 3.1 | −162.0 ± 5.1 |
| Cluster size | 34 | 28 | 47 |
| $\Delta G_{interaction}$ | −9.7 | −10.8 | −15.0 |
| $\Delta E_{electrostatic}$ | −175.9 ± 25.5 | −313.8 ± 29.8 | −625.7 ± 22.1 |
| $\Delta E_{VdW}$ | −59.4 ± 6.9 | −57.9 ± 2.1 | −86.3 ± 9.6 |
| $\Delta G_{desolvation}$ | −9.6 ± 9.9 | −5.1 ± 4.4 | 41.8 ± 9.3 |
| $K_d$ (M) | 5.9e−04 | 6.5e−08 | 9.2e−12 |
| Non-Interacting Surface (NIS) per property | | | |
| NIS charged % | 28.54 | 26.21 | 33.31 |
| NIS apolar % | 38.42 | 29.65 | 30.82 |

Referring to TABLE. 2, the IFNβ analog peptide may be most likely capable of binding to IFNAR1, with approximately similar binding energy compared to IFNβ. Also, the highly conserved peptide appears to have less IFNAR1 binding affinity than the IFNβ analog peptide due to lower $K_d$ value. Moreover, calculation of non-interacting surfaces implicated important role of electrostatic energies in the interaction selectivity of the peptides with IFNAR1. Therefore, the IFNβ analog peptide has higher interaction selectivity with IFNAR1 in comparison with the highly conserved peptide because the IFNβ analog peptide has lower percentage of charged non-interacting surface (NIS) and apolar NIS.

Example 4: Validation of Peptide-Receptor Interaction

In this example, validation of the IFNβ analog peptide-IFNAR1 complex as a peptide-receptor interaction was carried out using intrinsic fluorescence measurements. The IFNβ analog peptide had an amino acid sequence as set forth in SEQ ID No. 2. Fluorescence measurements could provide useful information including the binding of molecules to proteins at the molecular level. Intrinsic fluorescence of IFNAR1 would become significantly weakened if physicochemical conditions of local surroundings of IFNAR1 are changed slightly. For example, some factors such as biomolecule binding could be responsible for the weakening of the intrinsic fluorescence of IFNAR1.

In order to determine the quenching mechanism of the interaction between IFNAR1 and the IFNβ analog peptide, the fluorescence studies performed using a spectrofluorimeter with a cell compartment thermostated at 293 K. Protein intrinsic fluorescence experiments were carried out at constant IFNAR1 concentration titrated with different concentrations of IFNβ analog peptide to reach a maximum molar ratio of the IFNβ analog peptide-IFNAR1, and the complex maximum molar ratio of the IFNβ analog peptide-IFNAR1 was 10.

The concentration of IFNAR1 was 3 μM and the concentrations of the IFNβ analog peptide were from 0 to 30 μM in 50 mM phosphate buffer and pH 7.4 at 298 K. Emission spectra were recorded from 310 nm to 450 nm with an excitation wavelength of about 280 nm and at a scan rate of about 60 nm/min. The results of all fluorescence measurements were corrected by the results of the same titrations of medium without IFNAR1. Spectral resolution was 5 nm for both excitation and emission.

In these experiments, 1.0 ml solution with a fixed concentration of the IFNβ analog peptide was precisely added into the quartz cell with a 1 cm path length and was manually titrated by successive additions of the IFNβ analog peptide at 5 min time intervals. The fluorescence emission spectra were then measured, and the maximum fluorescence intensity at a wavelength of about 340 nm was used to calculate the binding constant parameters.

Figure 5A:
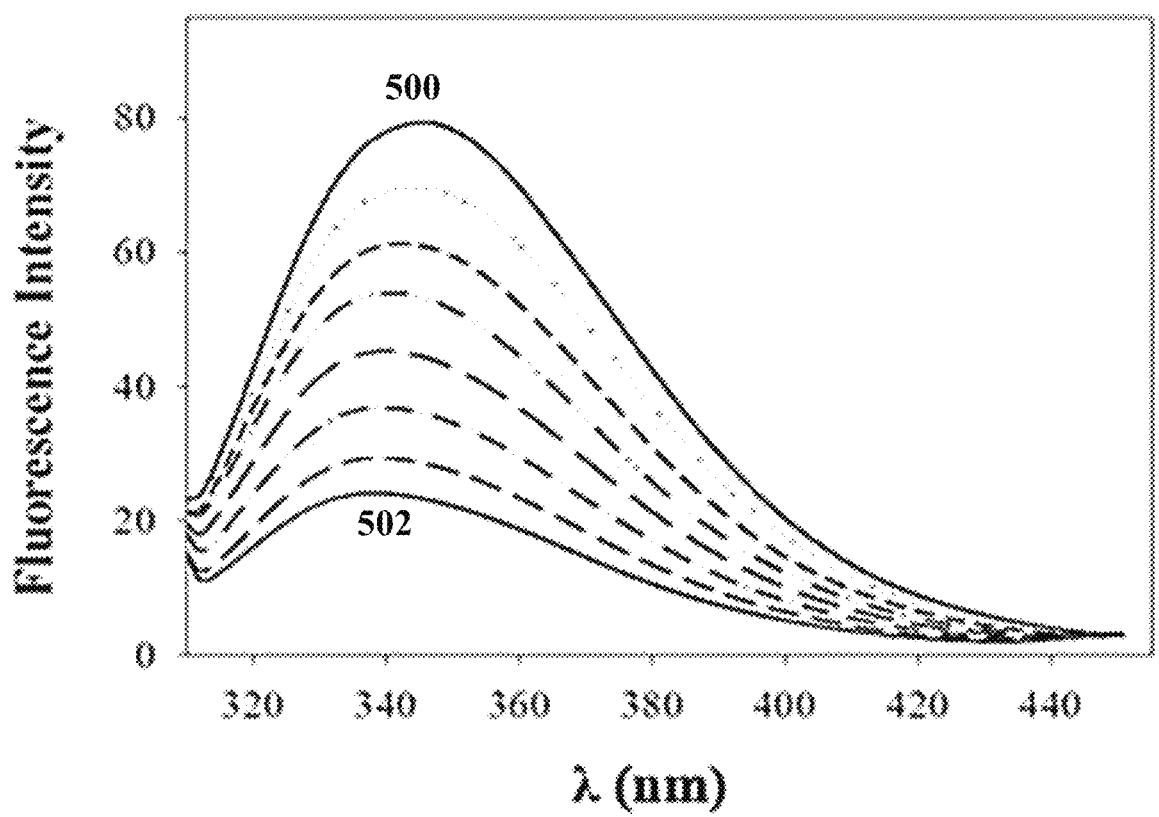
FIG. 5A illustrates fluorescence emission spectra of IFNAR1 at different concentrations of an IFNβ analog peptide, consistent with one or more exemplary embodiments of the present disclosure.

FIG. 5A shows fluorescence emission spectra of IFNAR1 at different concentrations of the IFNβ analog peptide, consistent with one or more exemplary embodiments of the present disclosure. Referring to FIG. 5A, the IFNAR1 fluorescence intensity quenched remarkably as the IFNβ analog peptide concentrations increased. This trend indicated the IFNβ analog peptide significantly interacts with IFNAR1 in a dose-dependent manner. The reduction in fluorescence intensity resulted from the diminution of the fluorescence quantum yield, which in turn was the result of a lowering of the electronic density after the IFNβ analog peptide interacted with the IFNAR1 as the receptor. This interaction caused the changes in the microenvironment of aromatic fluorophores of the IFNAR1.

Fluorescence quenching data from the interaction of the IFNβ analog peptide and IFNAR1 were analyzed to obtain various binding parameters. The binding constant ($K_a$) and the number of binding (n) were calculated according to the Eq. 1, where $F_0$ is the fluorescence emission intensities of IFNAR1 in the absence of the IFNβ analog peptide, F is the fluorescence emission intensities of IFNAR1 in the presence of the IFNβ analog peptide, [P] is the IFNβ analog peptide concentration, $K_a$ is the binding constant, and n is the apparent molar ratio of [IFNβ analog peptide]/[IFNAR1] complex.

$$\mathrm{Log}\frac{F_0 - F}{F} = \mathrm{Log}K_a + n\mathrm{Log}[P] \qquad \text{Eq. 1}$$

Figure 5B:
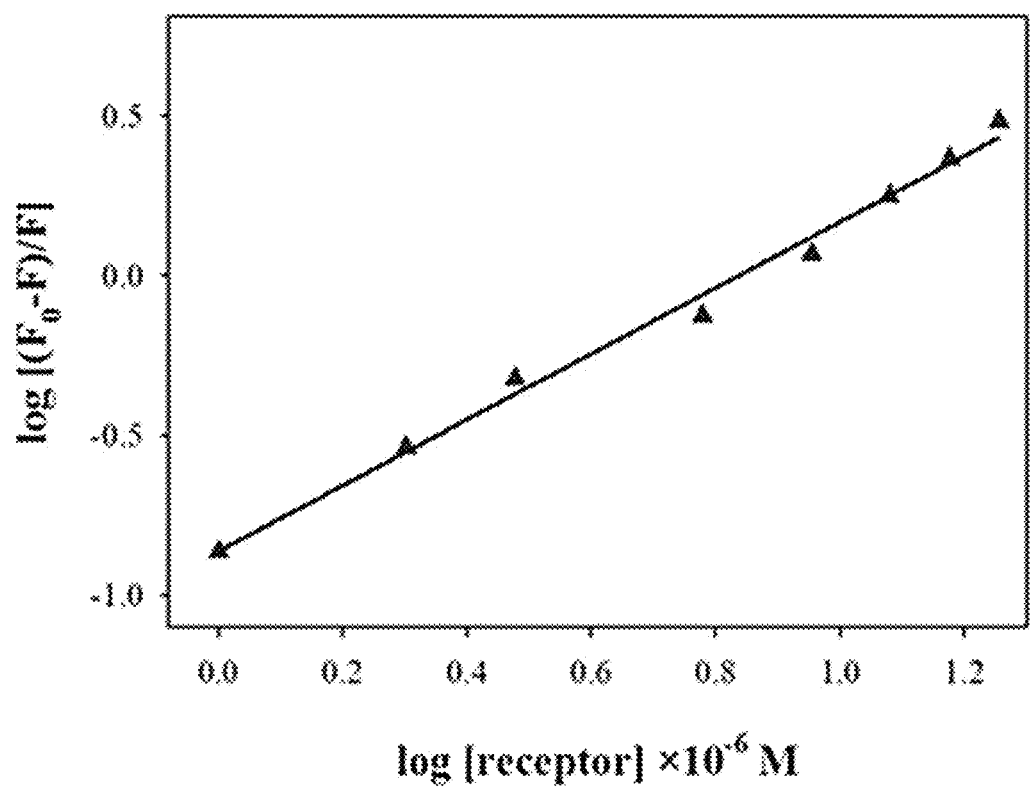
FIG. 5B illustrates a plot for quenching of IFNAR1 intrinsic fluorescent by an IFNβ analog peptide, consistent with one or more exemplary embodiments of the present disclosure.

FIG. 5B shows a plot for quenching of the IFNAR1 intrinsic fluorescent by the IFNβ analog peptide, consistent with one or more exemplary embodiments of the present disclosure. Referring to FIG. 5B, the slope of the straight-line equals to n as the number of bindings, and the intercept on Y-axis equal to log $K_a$. The values of $K_a$ and n at 298 K were $3.67(\pm 0.24) \times 10^7$ $M^{-1}$ and $1.17(\pm 0.09)$, respectively. The "n" and $K_a$ values indicated that IFNAR1 significantly interacts with the peptide and forms equimolar complex. It is evident from $K_a$ value that the binding of the IFNβ analog peptide to the IFNAR1 is enough strong to make a peptide-receptor inclusion complex.

Example 5: Therapeutic Effects of the IFNβ Analog Peptide

In this example, therapeutic effects of the IFNβ analog peptide with SEQ ID No. 1 on the development of progressive experimental autoimmune encephalomyelitis (EAE) were studied. At first, EAE was induced in 8 weeks old C57BL/6 male mice with a weight between 20 grams and 25 grams. In order to induce EAE, mice were anesthetized with isoflurane and subcutaneously injected with 100 μl of MOG (myelin oligodendrocyte glycoprotein) with a concentration of about 2.5 g/l suspended in 100 μl complete Freund's adjuvant (CFA) into the hind flank. Mice were also intraperitoneally injected with 400 ng of pertussis toxin in 200 μl of phosphate buffered saline (PBS). A second, identical injection of pertussis toxin was given two days following the first immunization. Injections were distributed over four spots, for example about 100 μl per site across the flank areas.

In order to investigate whether treatment with the IFNβ analog peptide could modulate the EAE, seven experimental groups were designed. One hundred and twenty-six mice were divided randomly into seven groups: (i) a vehicle group with 18 mice received injection of PBS solution as vehicle at day 14 of EAE induction, (ii) sham group with 18 mice received pertussis toxin without MOG; (iii) EAE groups with 90 mice received pertussis toxin with MOG and were divided into five separate subgroups (18 mice per subgroup), (iiia) without vehicle, the IFNβ analog peptide and IFNβ injection, (iiib) with 10 mg/kg body weight injection of the IFNβ analog peptide at day 14 of EAE induction (iiic) with 20 mg/kg body weight injection of the IFNβ analog peptide at day 14 of EAE induction (iiid) with 10 mg/kg body weight injection of IFNβ at day 14 of EAE induction (iiie) with 20 mg/kg body weight injection of IFNβ at day 14 of EAE induction.

In order to bypass the blood-brain barrier and other mechanisms that limit systemic drug distribution into the brain, intracerebroventricular injection (ICVI) route of administration was selected to allow CNS entrance of exact concentrations used for both IFNβ analog peptide and IFNβ. The immunized mice received intravenous injections of 100 μl containing IFNβ and the IFNβ analog peptide with doses of 0, 10 and 20 mg/kg dissolved in 0.2 M PBS into the right lateral ventricle of the mouse on day 14 of EAE induction.

After that, in order to conduct clinical evaluation, mice of the experimental groups were blinded scored as follows: score 0 for no overt signs of disease, score 1 for limp tail, score 2 for limp tail and hind limb weakness, score 3 for partial hind limb paralysis of one side (hemiparesis) or both sides (paraparesis), score 4 for complete hind limb paralysis of one side (hemiplegia) or both sides (paraplegia), score 5 for moribund state. The day of immunization was considered as EAE day 0 and clinical behavior of mice was scored daily. Mice were typically observed for 3 weeks, during which mice remained chronically paralyzed with the onset of paralysis between 12 and 16 days after immunization and a maximum score of 3 to 4 in most mice.

Figure 6:
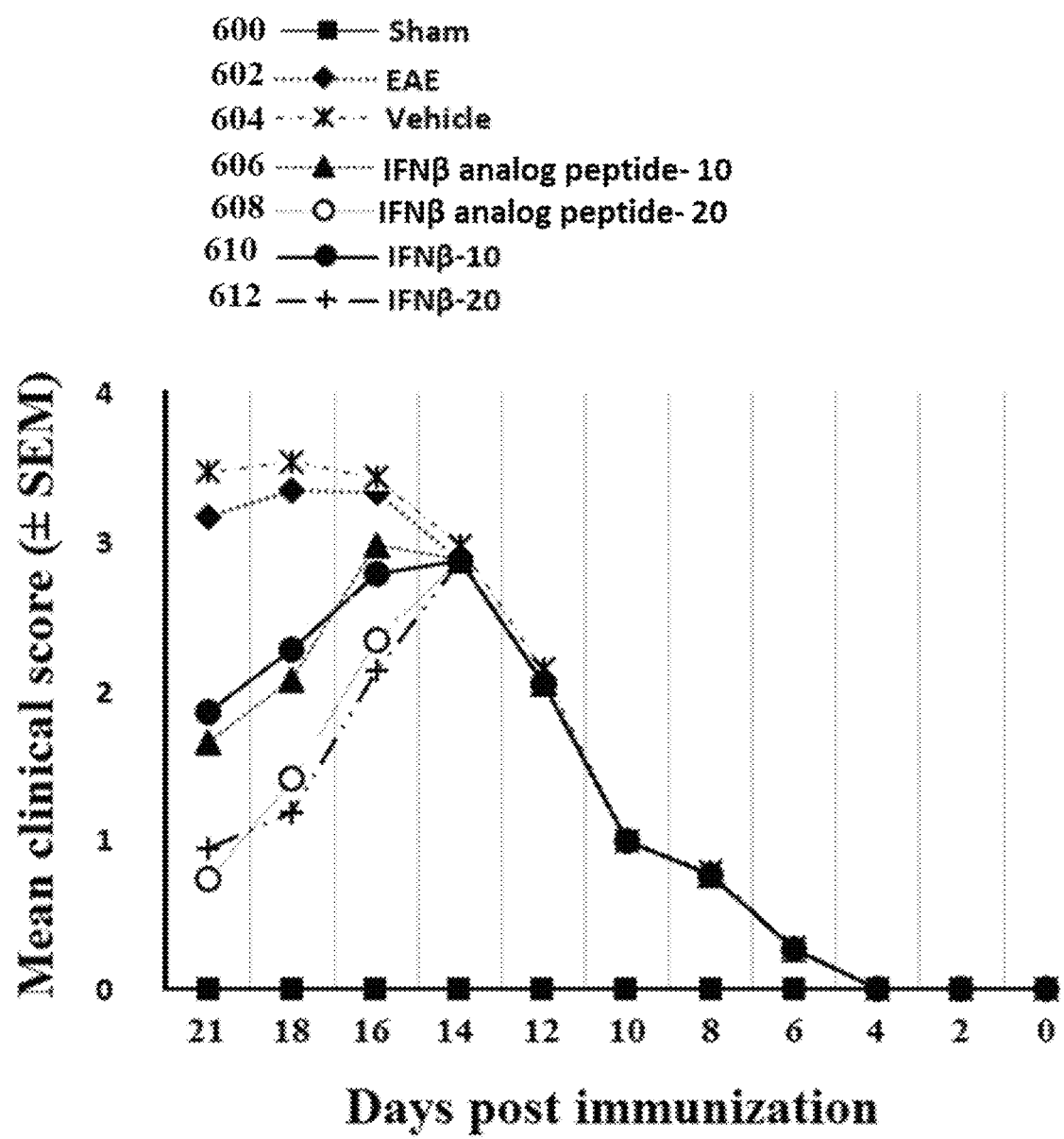
FIG. 6 illustrates mean clinical scores of different experimental groups after immunization, consistent with one or more exemplary of the present disclosure.

FIG. 6 shows mean clinical scores of different experimental groups after immunization, consistent with one or more exemplary embodiments of the present disclosure. The experimental groups were sham group treated with pertussis toxin without MOG 600, EAE-induced mice without any injection 602, EAE-induced mice treated with PBS solution as a vehicle group 604, EAE-induced mouse treated with 10 mg/kg IFNβ analog peptide 606, EAE-induced mice treated with 20 mg/kg IFNβ analog peptide 608, EAE-induced mice treated with 10 mg/kg IFNβ 610, EAE-induced mice treated with 20 mg/kg IFNβ 612. All of the treatments were done on day 14 post-immunization.

Referring to FIG. 6, comparison area under curve (AUC) between IFNβ analog peptide-treated groups 606 and 608 and control groups of vehicle group 604 and EAE group 602 revealed that the IFNβ analog peptide-treated groups 606 and 608 showed a higher decrease in mean clinical score, and IFNβ analog peptide treatment significantly attenuated severity of clinical EAE (P<0.05 and P<0.01). Therefore, it may be concluded that IFNβ analog peptide had a modulatory effect on EAE progression. The IFNβ analog peptide could efficiently bind to IFNAR1 and suppress neuroinflammation in-vivo. Also, IFNβ analog peptide had protective effects against MOG-induced EAE via reduction of immune dysfunction and inflammation.

Referring again to FIG. 6, as expected, IFNβ-treated groups 610 and 612 showed a significant reduction in the clinical score in comparison with control groups of vehicle group 604 and EAE group 602. Comparison between IFNβ analog peptide-treated groups 606 and 608 and IFNβ-treated groups 610 and 612 showed that there was no statistically significant difference between effects of IFNβ analog peptide and IFNβ on changes in clinical scores during treatments, and a significant amelioration in clinical severity was observed for both IFNβ-treated groups and IFNβ analog peptide-treated groups in a time-dependent manner.

Referring again to FIG. 6, comparison between EAE-induced mouse treated with 10 mg/kg IFNβ analog peptide 606 and EAE-induced mice treated with 20 mg/kg IFNβ analog peptide 608 indicates that raising the dose of the IFNβ analog peptide could further protect mice from EAE clinical symptoms. In addition, an increased in drug dosage for both IFNβ and IFNβ analog peptide improved disease protection with the same pattern.

Example 6: Effects of the Ifnβ Analog Peptide on Inflammation Mediators

In this example, effects of the IFNβ analog peptide as the IFNβ analog peptide on the expression of some related inflammations mediators such as matrix metalloproteinase 2 (MMP2) and matrix metalloproteinase 9 (MMP9) were studied using quantitative real-time polymerase chain reaction (PCR).

Figure 7A:
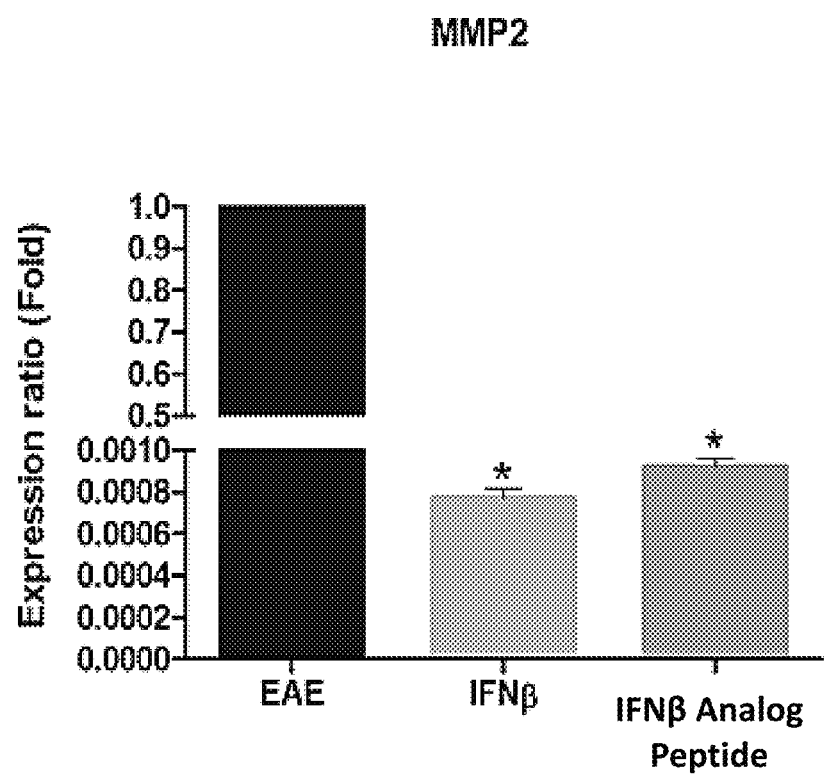
FIG. 7A illustrates an expression fold change of matrix metalloproteinase 2 (MMP2) in IFNβ analog peptide-treated mice and IFNβ-treated mice, consistent with one or more exemplary embodiments of the present disclosure.
Figure 7B:
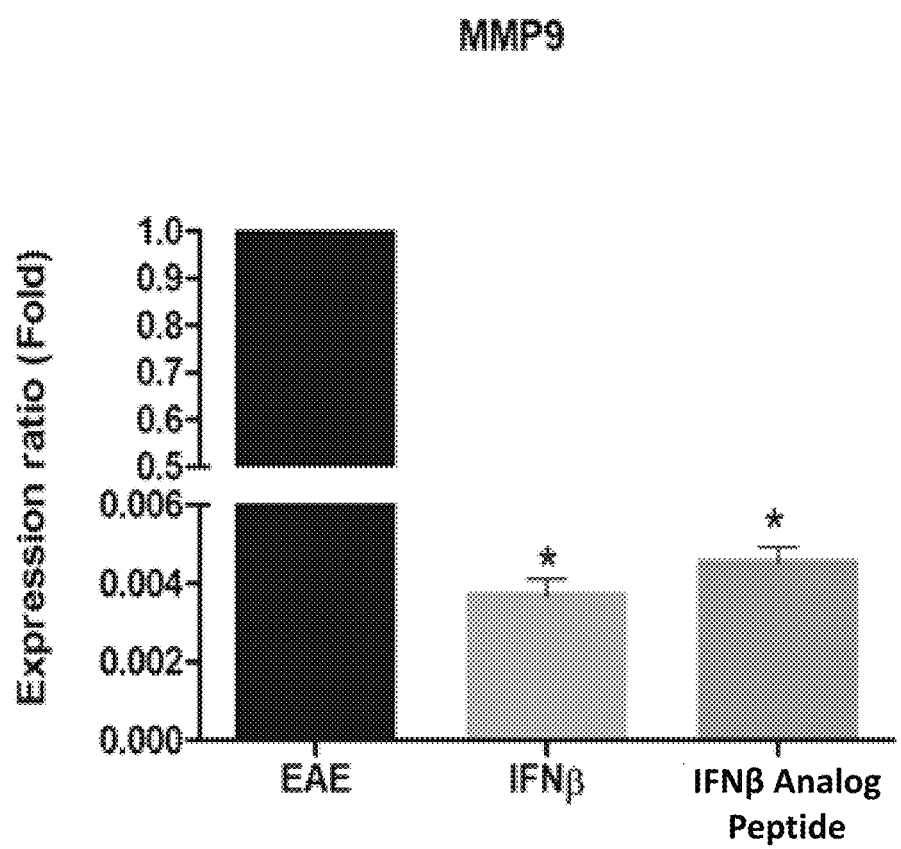
FIG. 7B illustrates an expression fold change of matrix metalloproteinase 9 (MMP9) and MMP2 in IFNβ analog peptide-treated mice and IFNβ-treated mice, consistent with one or more exemplary embodiments of the present disclosure.

FIG. 7A shows an expression fold change of matrix metalloproteinase 2 (MMP2) in IFNβ analog peptide-treated mice and IFNβ-treated mice, consistent with one or more exemplary embodiments of the present disclosure. FIG. 7B shows an expression fold change of matrix metalloproteinase 9 (MMP9) and MMP2 in IFNβ analog peptide-treated mice and IFNβ-treated mice, consistent with one or more exemplary embodiments of the present disclosure. The EAE mice were treated with PBS as the vehicle group, and dosage of the IFNβ analog peptide and IFNβ was 20 mg/kg in IFNβ analog peptide-treated mice and IFNβ-treated mice groups. After that RNA of the cells was extracted and their cDNA was synthesized.

Referring to FIGS. 7A and 7B, treatment with IFNβ analog peptide and IFNβ showed a significant decrease in MMP2 and MMP9 gene expression fold change in the brain tissue compared to the vehicle group (P<0.05). 0.05). However, reduction of these inflammation mediators was more in IFNβ-treated mice.

Moreover, after 21 days of EAE induction, mice were euthanized and their blood was obtained via cardiac puncture and plasma was prepared. Expression levels of tumor necrosis factor-alpha (TNFα) and interleukin 1β (IL1β) as circulating inflammatory biomarkers were measured in the plasma using quantitative enzyme-linked immunosorbent assay (ELISA) kits.

Figure 7C:
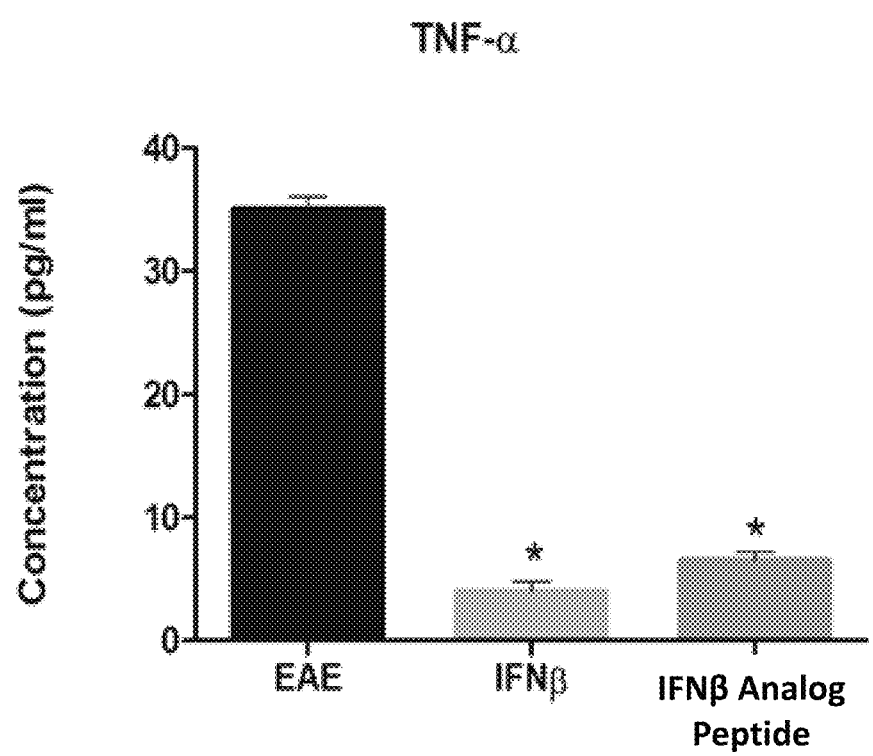
FIG. 7C illustrates a concentration change of tumor necrosis factor alpha (TNFα) in IFNβ analog peptide-treated mice and IFNβ-treated mice, consistent with one or more exemplary embodiments of the present disclosure.
Figure 7D:
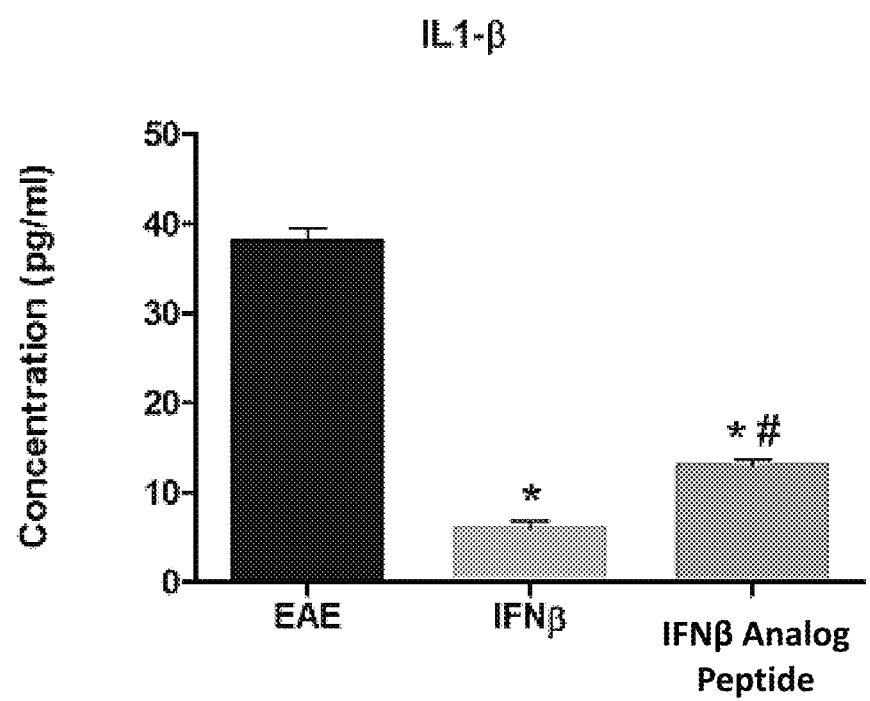
FIG. 7D illustrates a concentration change of interleukin 1 beta (IL1β) in IFNβ analog peptide-treated mice and IFNβ-treated mice, consistent with one or more exemplary embodiments of the present disclosure.

FIG. 7C shows a concentration change of tumor necrosis factor alpha (TNFα) in IFNβ analog peptide-treated mice and IFNβ-treated mice, consistent with one or more exemplary embodiments of the present disclosure. FIG. 7D shows a concentration change of interleukin 1 beta (IL1β) in IFNβ analog peptide-treated mice and IFNβ-treated mice, consistent with one or more exemplary embodiments of the present disclosure. Referring to FIGS. 7C and 7D, treatment with IFNβ analog peptide and IFNβ showed a significant decrease in plasma levels of TNFα and IL1β compared to the vehicle group (P-value<0.05). However, reduction of these inflammation mediators was more in IFNβ-treated mice.

Furthermore, brain inflammatory response after IFNβ analog peptide treatment as the IFNβ analog peptide was evaluated by measuring the number of IL-17 positive cells, CD11b positive cells, and CD45 positive cells. IL-17 is the most important pro-inflammatory cytokine produced by T-helper cells, CD11b is an activated macrophages and microglia marker, and CD45 is a general leukocytes marker.

Figure 8A:
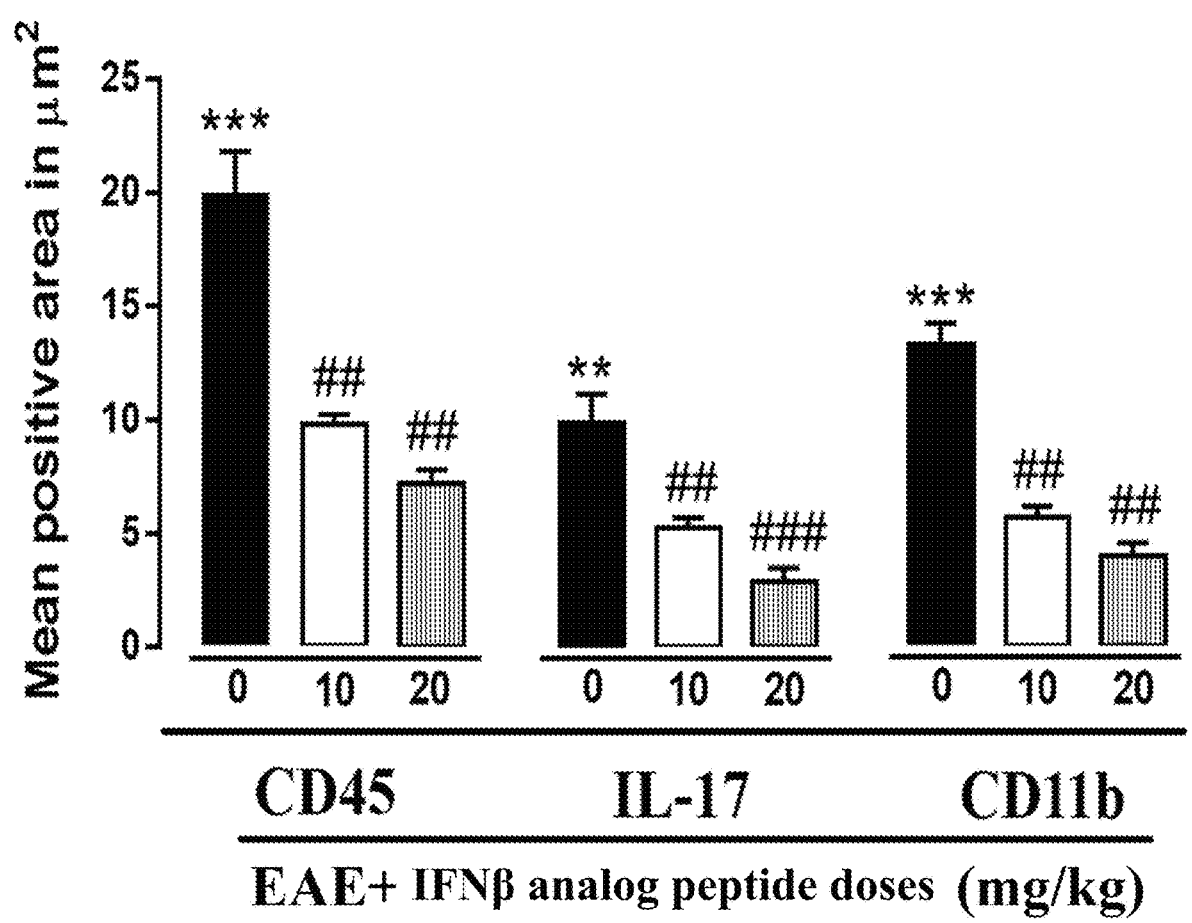
FIG. 8A illustrates a percentage of interleukin 17 (IL17) positive cells, cluster of differentiation 11b (CD11b) positive cells, and cluster of differentiation 45 (CD45) positive cells in each μm2 of mice cerebral cortex after injection of an IFNβ analog peptide, consistent with one or more exemplary embodiments of the present disclosure.

After 21 days of EAE induction, mice were euthanized and were transcardially perfused with PBS. Then, the brains were dissected; cerebral cortex was isolated and snap-frozen in liquid nitrogen. FIG. 8A shows a percentage of interleukin 17 (IL17) positive cells, cluster of differentiation 11b (CD11b) positive cells, and cluster of differentiation 45 (CD45) positive cells in each μm2 of mice cerebral cortex after injection of an IFNβ analog peptide, consistent with one or more exemplary embodiments of the present disclosure.

Referring to FIG. 8A, there is a significant reduction of IL-17, CD11b, and CD45 in the cerebral cortex after IFNβ analog peptide treatment, particularly in the higher dosage, for example, 20 mg/kg. Quantitative analysis revealed that this reduction occurs in a dose-dependent manner. The percentage of IL-17, CD11b and CD45 positive cells in the mice treated with 20 mg/kg of IFNβ analog peptide was all less than half of the untreated EAE mice, and the most significant decrease was observed for CD45, especially when 20 mg/kg of IFNβ analog peptide was applied.

Figure 8B:
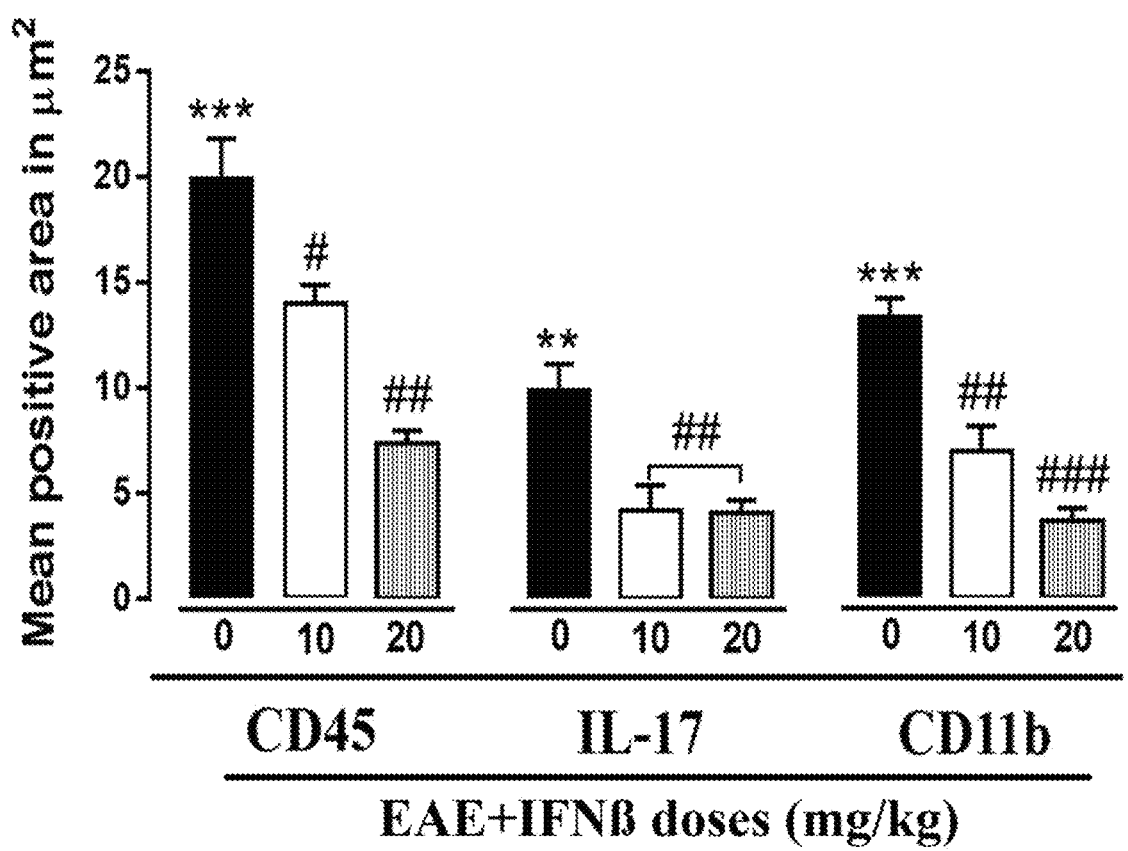
FIG. 8B illustrates a percentage of IL17, CD11b and CD45 positive cells in each $\mu m^2$ of mice cerebral cortex after IFNβ injection, consistent with one or more exemplary embodiments of the present disclosure.

FIG. 8B shows a percentage of IL17, CD11b and CD45 positive cells in each $\mu m^2$ of mice cerebral cortex after IFNβ injection, consistent with one or more exemplary embodiments of the present disclosure. Referring to FIG. 8B, the percentage of IL-17, CD11b, and CD45 positive cells were considerably decreased in mice treated with IFNβ, particularly in the 20 mg/kg dosage.

Referring again to FIGS. 8A and 8B, there was no statistically significant difference between effects of the IFNβ analog peptide and IFNβ on the expression of IL-17, CD11b, and CD45 during treatments. In-vivo analyses revealed that the IFNβ analog peptide could lessen inflammation of the EAE mice by modulating the levels of inflammatory mediators.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. An interferon-beta (IFNβ) analog peptide, the IFNβ analog peptide has an amino acid sequence as set forth in SEQ ID No. 1.

2. The IFNβ analog peptide according to claim 1, wherein the IFNβ analog peptide has an antiviral activity and an immunomodulatory activity, wherein the immunomodulatory activity comprises suppressing pro-inflammation mediators.

3. An interferon-beta (IFNβ) analog peptide, the IFNβ analog peptide has an amino acid sequence as set forth in SEQ ID No. 3.

4. The IFNβ analog peptide according to claim 3, wherein the IFNβ analog peptide has an antiviral activity and an immunomodulatory activity, wherein the immunomodulatory activity comprises suppressing pro-inflammation mediators.

* * * * *

SEQUENCE LISTING

```
<160> NUMBER OF SEQ ID NOS: 4

<210> SEQ ID NO 1
<211> LENGTH: 27
<212> TYPE: PRT
<213> ORGANISM: Artificial Sequence
<220> FEATURE:
<223> OTHER INFORMATION: Synthetic sequence

<400> SEQUENCE: 1

Met Leu Gln Asn Phe Arg Ala Gly Trp His Gln Asn Thr Leu Asn Thr
1               5                   10                  15

Gly Leu Arg Trp Val Gly Phe Glu Asn Leu Leu
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetic sequence

<400> SEQUENCE: 2

Met Leu Gln Asn Gly Arg Asp Val Arg Lys Arg Gly Phe Ser Asp Thr
1               5                   10                  15

Gly Leu Arg Lys Leu Gly Arg Val Asn Leu Leu
            20                  25

<210> SEQ ID NO 3
<211> LENGTH: 27
<212> TYPE: PRT
<213> ORGANISM: Artificial Sequence
```

-continued

```
<220> FEATURE:
<223> OTHER INFORMATION: Synthetic sequence

<400> SEQUENCE: 3

Met Leu Gln Asn Gly Arg Ala Leu Arg Lys Gln Asn Phe Leu Asn Thr
1               5                   10                  15

Gly Leu Arg Lys Leu Gly His Glu Asn Leu Leu
            20                  25

<210> SEQ ID NO 4
<211> LENGTH: 27
<212> TYPE: PRT
<213> ORGANISM: Homo sapiens

<400> SEQUENCE: 4

Met Leu Gln Asn Ile Phe Ala Ile Phe Arg Gln Asp Ser Ser Ser Thr
1               5                   10                  15

Gly Trp Asn Glu Thr Ile Val Glu Asn Leu Leu
            20                  25
```